United States Patent
Fish et al.

(10) Patent No.: US 9,526,420 B2
(45) Date of Patent: Dec. 27, 2016

(54) MANAGEMENT, CONTROL AND COMMUNICATION WITH SENSORS

(71) Applicant: Nortek Security & Control LLC, Carlsbad, CA (US)

(72) Inventors: Ram David Adva Fish, Menlo Park, CA (US); Henry Messenger, Campbell, CA (US)

(73) Assignee: Nortek Security & Control LLC, Carlsbad, CA (US)

( * ) Notice: Subject to any disclaimer, the term of this patent is extended or adjusted under 35 U.S.C. 154(b) by 279 days.

(21) Appl. No.: 14/062,688

(22) Filed: Oct. 24, 2013

(65) Prior Publication Data

US 2014/0118159 A1 May 1, 2014

Related U.S. Application Data

(60) Provisional application No. 61/719,277, filed on Oct. 26, 2012.

(51) Int. Cl.
| | |
|---|---|
| G08C 19/16 | (2006.01) |
| G06F 17/30 | (2006.01) |
| G06F 3/00 | (2006.01) |
| G06Q 10/00 | (2012.01) |
| A61B 5/00 | (2006.01) |
| G08C 17/02 | (2006.01) |
| H04Q 9/00 | (2006.01) |
| A61B 5/0205 | (2006.01) |
| A61B 5/11 | (2006.01) |
| G08C 17/00 | (2006.01) |

(52) U.S. Cl.
CPC ........... *A61B 5/0022* (2013.01); *A61B 5/6801* (2013.01); *G08C 17/02* (2013.01); *H04Q 9/00* (2013.01); *A61B 5/02055* (2013.01); *A61B 5/1112* (2013.01); *A61B 5/747* (2013.01); *A61B 2560/0266* (2013.01); *G08C 17/00* (2013.01); *G08C 2201/31* (2013.01)

(58) Field of Classification Search
CPC ...... A61B 5/0022; A61B 5/747; A61B 5/6801
USPC ..................................................... 340/870.01
See application file for complete search history.

(56) References Cited

U.S. PATENT DOCUMENTS

| | | |
|---|---|---|
| 2004/0172290 A1 | 9/2004 | Leven |
| 2009/0073991 A1 | 3/2009 | Landrum et al. |
| | (Continued) | |

FOREIGN PATENT DOCUMENTS

| | | |
|---|---|---|
| WO | 2008098346 | 8/2008 |

OTHER PUBLICATIONS

International Search Report for and Written Opinion of the International Searching Authority for International Patent Application No. PCT/US13/66966 dated Jan. 17, 2014, 11 pages.

(Continued)

*Primary Examiner* — Jennifer Mehmood
*Assistant Examiner* — John Mortell
(74) *Attorney, Agent, or Firm* — Schwegman Lundberg & Woessner, P.A.

(57) ABSTRACT

A voice call is established using a computing device. A user is instructed to prepare a first device for pairing with the computing device and a server may instruct the computing device to scan for additional devices. The server may identify a first device from a list of devices and may instruct the computing device to pair with the first device.

20 Claims, 6 Drawing Sheets

(56) References Cited

U.S. PATENT DOCUMENTS

| | | | |
|---|---|---|---|
| 2010/0318578 A1* | 12/2010 | Treu | G06F 19/3418 707/802 |
| 2011/0090086 A1 | 4/2011 | Dicks et al. | |
| 2012/0083237 A1 | 4/2012 | Fish et al. | |
| 2012/0108917 A1* | 5/2012 | Libbus | A61B 5/0006 600/301 |
| 2012/0182939 A1 | 7/2012 | Rajan et al. | |
| 2012/0185267 A1 | 7/2012 | Kamen et al. | |
| 2012/0266251 A1 | 10/2012 | Birtwhistle et al. | |
| 2013/0141235 A1 | 6/2013 | Utter, II | |

OTHER PUBLICATIONS

European Application Serial No. 13848885.3, Extended European Search Report mailed Oct. 10, 2016, 9 pgs.

\* cited by examiner

MANAGEMENT, CONTROL AND COMMUNICATION WITH SENSORS

CROSS-REFERENCE TO RELATED APPLICATION

This application claims the benefit of U.S. Provisional Patent Application No. 61/719,277 filed Oct. 26, 2012, the contents of which are hereby incorporated by reference in their entirety.

TECHNICAL FIELD

Embodiments of the present invention relate generally to health care-based monitoring systems, and more specifically, to mechanisms for managing, controlling, and communicating data between devices.

BACKGROUND

For certain age groups, such as the elderly, or people that engage in certain dangerous activities, such as firefighters and soldiers, it is desirable to track and understand human activity automatically. For example, a person that has fallen may be injured, unconscious, etc., and needs emergency assistance. In such circumstances, relying on the person to initiate a call to a public safety access point (PSAP) (e.g., 9-1-1 emergency services, an automated emergency call center, etc.) is not practical. Moreover, even if the person is capable of placing the call, the PSAP may be located outside the geographical jurisdiction for providing emergency services. An emergency services person located at a PSAP may need to manually place a second call to the local fire station, police, or Emergency Medical Services (EMS) squad, thereby wasting precious time that could be used to save the person's life. Further, if the person is unconscious, they would not be able to relate the nature of their injuries nor their physical location.

A wearable device may be worn by the user and the wearable device may monitor the activities and/or health of the user using a variety of sensors and/or components (e.g., GPS units, a blood pressure unit, an accelerometer, etc.). The wearable device may also provide a simple interface (e.g., a single button) to allow a user to initiate a voice call (e.g., to request help). However, these simplified interfaces (e.g., the single button) may not allow a user to choose a destination for the voice call. The wearable device may be configured to call a single destination (e.g., a PSAP) in response to a user request (e.g., in response to the user pushing the button) and may not be able to initiate voice calls to other destinations in response to the user request. The wearable device may use various other devices (e.g., health sensors). For example, the wearable device may user a blood pressure sensor, a thermometer, a weight sensor (e.g., a scale), etc., to monitor the condition, health and/or state of the user.

BRIEF DESCRIPTION OF THE DRAWINGS

Embodiments of present invention will be more readily understood from the detailed description of exemplary embodiments presented below considered in conjunction with the attached drawings.

DETAILED DESCRIPTION

As discussed above, a wearable device may use various other devices (e.g., health sensors). For example, the wearable device may use a blood pressure sensor, a thermometer, a weight sensor (e.g., a scale), etc., to monitor the condition, health and/or state of the user. Users may not be familiar with the procedures, operations, commands, etc., that may be needed to pair the wearable device with each of the other devices. For example, each type of health sensor may have a different procedure and/or passwords for pairing the health sensor with the wearable device.

Embodiments of the invention provide mechanisms for pairing devices such that the devices may communicate data. A wearable device may be paired with other devices (e.g., health sensors). A user may use the wearable device to establish a voice call with a remote operator in a call center. The remote operator may instruct the user to prepare a first device for pairing with the wearable device. After the user has prepared the device for pairing, the remote operator may use a server to pair the wearable device with the first device. The server may instruct the wearable device to activate/power up a communication interface and to scan for devices. The wearable device may provide a list of devices that are visible to the wearable device. The server may receive input identifying the first device from the list of devices and may provide instructions to the wearable device for pairing the first device with the wearable device. Some embodiments may allow the server to pair the wearable device with the first device automatically (e.g., without input and/or intervention from the user). This may allow users to pair a wearable device with other devices (e.g., health sensors) more quickly and efficiently.

In one embodiment, the wearable device may operate as a tunnel and may forward data from the wearable device to the server and vice versa. This may allow the wearable device to pair with devices when the wearable device is not able understand and/or process the data and/or information from these devices. The wearable device may forward the data to the server and the server may process the data, instead of having the wearable device process the data. The other devices (e.g., the other health sensors) may receive data from the server and may process the data (e.g., commands, etc.) from the server, instead of having the wearable device process the data.

Figure 1:
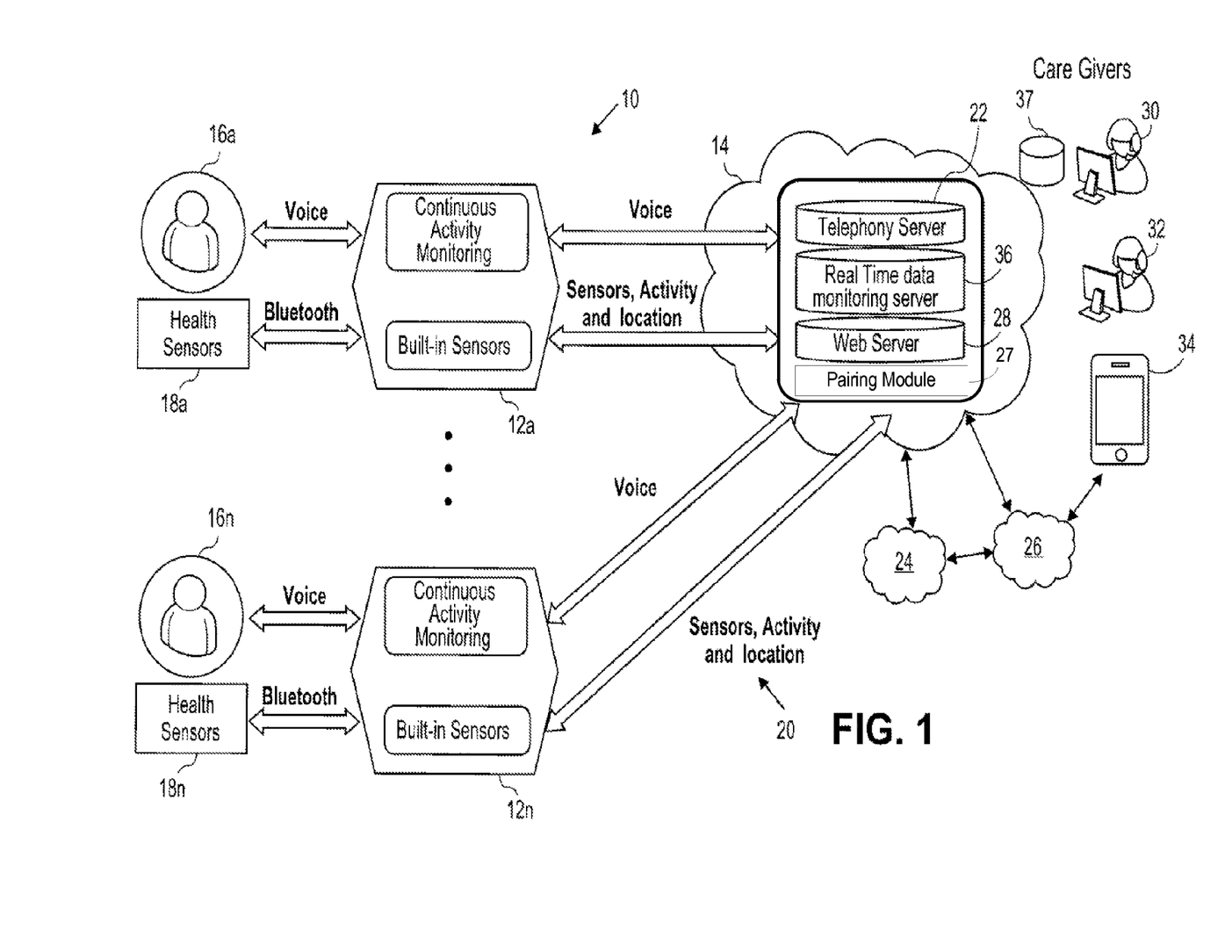
FIG. 1 is a block diagram illustrating one embodiment of a system for detecting a predefined user state, according to one embodiment of the present disclosure.

FIG. 1 is a block diagram illustrating one embodiment of a system 10 for detecting a predefined user state. The system 10 includes wearable devices 12a-12n communicatively connected to a distributed cloud computing system 14. A wearable device 12 may be a small-size computing device that can be worn as a watch, a pendant, a ring, a pager, or the like, and can be held in any orientation.

In one embodiment, each of the wearable devices 12a-12n is operable to communicate with a corresponding one of users 16a-16n (e.g., via a microphone, speaker, and voice recognition software), external health sensors 18a-18n (e.g., an EKG, blood pressure device, weight scale, glucometer) via, for example, a short-range over the air (OTA) transmission method (e.g., Bluetooth, Wi-Fi, etc.), a call center 30, a first-to-answer system 32, and care giver and/or family member 34, and the distributed cloud computing system 14 via, for example, a long range OTA transmission method (e.g., over a $3^{rd}$ Generation (3G) or $4^{th}$ Generation (4G) cellular transmission network 20, such as a Long Term Evolution (LTE) network, a Code Division Multiple Access (CDMA) network, etc.).

Each wearable device 12 is configured to detect a predefined state of a user. The predefined state may include a user physical state (e.g., a user fall inside or outside a building, a user fall from a bicycle, a car incident involving a user, a user taking a shower, etc.) or an emotional state (e.g., a user screaming, a user crying, etc.). As will be discussed in more detail below, the wearable device 12 may include multiple sensors for detecting a predefined user state. For example, the wearable user device 12 may include an accelerometer for measuring an acceleration of the user, a magnetometer for measuring a magnetic field associated with the user's change of orientation, a gyroscope for providing a more precise determination of orientation of the user, and a microphone for receiving audio. Based on data received from the above sensors, the wearable device 12 may identify a suspected user state, and then categorize the suspected user state as an activity of daily life, a confirmed predefined user state, or an inconclusive event. The wearable user device 12 may then communicate with the distributed cloud computing system 14 to obtain a re-confirmation or change of classification from the distributed cloud computing system 14. In another embodiment, the wearable user device 12 transmits data provided by the sensors to the distributed cloud computing system 14, which then determines a user state based on this data.

In one embodiment, the wearable device 12 includes a low-power processor (e.g., low-power processing device) to process data receive from sensors and/or detect anomalous sensor inputs. The low-power processor may cause a second processing device to further analyze the sensor inputs (e.g., may wake up a main CPU). If the second processing device determines that there is possibly an anomalous event in progress the second processing device may send dataset to the distributed cloud computing system 14. In one embodiment, if the distributed cloud computing system 14 concludes there is an anomalous event, the distributed cloud computing system 14 may instruct the wearable device 12 to initiate a voice call.

In one embodiment, the wearable user device 12 may also obtain audio data from one or more microphones on the wearable device 12. For example, the wearable user device 12 may record the user's voice and/or sounds which are captured by the one or more microphones, and may provide the recorded sounds and/or voice to the distributed cloud computing system 14 for processing (e.g., for voice or speech recognition).

In one embodiment, the wearable devices 12a-12n may continually or periodically gather/obtain data from the sensors and/or the one or more microphones (e.g., gather/obtain datasets and audio data) and the wearable devices 12a-12n may transmit these datasets to the distributed cloud computing system 14. The datasets may be transmitted to the distributed cloud computing system 14 at periodic intervals, or when a particular event occurs (e.g., user pushes a button on the wearable device 12a-12n or a fall is detected). In one embodiment, the datasets may include data indicative of measurements or information obtained by the sensors which may be within or coupled to the wearable device 12a-12n. For example, the datasets may include temperature readings (e.g., 98.5 degrees Fahrenheit, measurements obtained from an accelerometer (e.g., a rate of acceleration), a GPS location (e.g., GPS or longitude/latitude coordinates), etc. In one embodiment, the wearable device 12a-12n may transmit a dataset per sensor (e.g., one dataset for the accelerometer, one data set for an aGPS receiver, etc.) In another embodiment, the wearable device 12a-12n may combine data received from multiple sensors into a dataset.

Cloud computing provides computation, software, data access, and storage services that do not require end-user knowledge of the physical location and configuration of the system that delivers the services. The term "cloud" refers to one or more computational services (e.g., servers) connected by a computer network.

The distributed cloud computing system 14 may include one or more computers configured as a telephony server 22 communicatively connected to the wearable devices 12a-12n, the Internet 24, and one or more cellular communication networks 20, including, for example, the public circuit-switched telephone network (PSTN) 26. The distributed cloud computing system 14 may further include one or more computers configured as a Web server 28 communicatively connected to the Internet 24 for permitting each of the users 16a-16n to communicate with a call center 30, first-to-answer systems 32, and care givers and/or family 34. The web server 28 may also provide an interface for users to interact with the distributed cloud computing system 14 (e.g., to access their accounts, profiles, or subscriptions, to access stored datasets and/or audio data, etc.) The distributed cloud computing system 14 may further include one or more computers configured as a real-time data monitoring and computation server 36 communicatively connected to the wearable devices 12a-12n for receiving measurement data (e.g., datasets), for processing measurement data to draw conclusions concerning a potential predefined user state, for transmitting user state confirmation results and other commands back to the wearable devices 12a-12n, for storing and retrieving present and past historical predefined user state data from a database 37 which may be employed in the user state confirmation process, and in retraining further optimized and individualized classifiers that can in turn be transmitted to the wearable device 12a-12n. In one embodiment, the web server 28 may store and retrieve present and past historical predefined user state data, instead of the real-time data monitoring and computation serve 36 or the database 37.

In one embodiment, the wearable devices 12a-12n may include a button, which a user 16 may use to initiate voice calls. For example, a user 16a may push the button on the device 12a to initiate a voice call in order to obtain assistance or help (e.g., because the user has slipped or fallen, or because the user requires medical assistance). As discussed above, the wearable devices 12a-12n may periodically transmit datasets to the distributed cloud computing system 14. In one embodiment, the wearable devices 12a-12n may also transmit datasets to the distributed cloud computing system 14 when the user press or pushes the button on the wearable devices 12a-12n. In one embodiment, the wearable devices 12a-12n may be single-button devices (e.g., devices which only have one button) which provide a simplified interface to users.

In one embodiment, the distributed cloud computing system 14 may receive a request from the wearable device 12a-12n to initiate the voice call. The distributed cloud computing system 14 may also receive datasets from the wearable device 12a-12n associated with an event experienced by the user. After receiving the request to initiate the voice call, the distributed cloud computing system 14 may analyze the datasets to determine whether the event experienced by the user is an activity of daily life (ADL), a confirmed fall, or an inconclusive event. In another embodiment, the distributed cloud computing system 14 may identify a destination for routing the voice call, based on the analysis of the datasets. For example, if the distributed cloud computing system 14 analyzes the datasets and determines that the event is a confirmed fall, the distributed cloud computing system 14 may identify a first-to-answer system 32 (e.g., a 911 or emergency response call center) as destination for the voice call. In another example, if the distributed cloud computing system 14 analyzes the datasets and is unable to determine what event occurred (e.g., an inconclusive event), the distributed cloud computing system 14 may identify a family member 24, as destination for the voice call. After identifying a destination for the voice call, the distributed cloud computing system 14 routes the voice call to the identified destination.

In one embodiment, the distributed cloud computing system 14 may also analyze audio data received from a wearable device 12 to determine what event has happened to a user. For example, the wearable device 12 may provide audio data (e.g., a recording of the user's voice or other sounds) to the distributed cloud computing system 14. The distributed cloud computing system 14 may analyze the sound data and may determine that a user is asking for help (e.g., based on the user's words in the recording). The distributed cloud computing system 14 may identify a destination for the voice call, based on the audio data and/or the datasets received from the wearable device 12 and may route the voice call to the identified destination. The audio data may be used in conjunction with the datasets to identify a destination for routing the voice call.

In one embodiment, the distributed cloud computing system 14 may monitor the status of the voice call, after it routes the voice call to the identified destination. For example, the distributed cloud computing system 14 may route the voice call to a first destination and may route the call to a second destination if the call is not answered by the first destination. In another embodiment, the distributed cloud computing system 14 may also use subscription data (e.g., information associated with a user's account or subscription to a service) to identify destinations for routing the voice call. For example, the subscription data may include a list and/or an order for destinations where the voice call should be routed. In a further embodiment, the distributed cloud computing system 14 may also use a time of day and/or a geographic location to identify destinations for routing a voice call. For example, based on certain times of data and/or based on the location of the wearable device, the distributed cloud computing system 14 may route the voice to different locations.

The distributed cloud computing system 14 also includes a pairing module 27. The pairing module 27 may allow the distributed cloud computing system 14 to pair health sensors (e.g., health sensor 18a) with wearable devices (e.g., wearable device 12a). Pairing a health sensor to a wearable device may refer to establishing one or more communication channels between the health sensor and the wearable device (e.g., a physical communication channel or a logical communication channel). Pairing a health sensor to a wearable device may also refer to storing an identifier for the wearable device on the health sensor and/or storing an identifier for the health sensor on the wearable device. For example, the wearable device 12a may store an identifier for the health sensor 18a to indicate that the wearable device 12a is allowed to create a communication channel with the health sensor 18a and to communicate data with the health sensor 18a. Pairing a health sensor to a wearable device allows the health sensor and the wearable device to communicate data between the health sensor and the wearable device (e.g., sensor data, messages, information, etc.) using the one or more communication channels. One example of pairing may be pairing two Bluetooth capable devices. (e.g., Bluetooth pairing). Although some embodiments described herein may refer to Bluetooth and/or Bluetooth pairing, other embodiments may use different communication channels, different communication protocols, and/or different communication interfaces to pair a health sensor to a wearable device. For example, the wearable device may be paired with the health sensor using protocols and/or channels such as ZigBee, Z-Wave, RuBee, 802.15, 802.11, transmission control protocol/internet protocol (TCP/IP), user datagram protocol (UDP), and/or other communication protocols.

As discussed above, a user (e.g., user 16a) may acquire additional devices, such as medical sensors, to monitor the state, condition, and/or health of the user. For example, the user may request and/or order an additional health sensor (e.g., a weigh scale). In another example, a caregiver or a doctor of the user may request and/or order the additional health sensor. Examples of health sensors include, but are not limited to, an EKG, a blood pressure sensor, a weight scale, an inertial measurement unit, a pressure sensor for measuring air pressure or altitude, a heart rate sensor, a blood perfusion sensor, a temperature sensor (e.g., a thermometer), a glucose level sensor (e.g., a glucometer), etc. When the user receives the health sensor (or other device), the health sensor may be paired with a wearable device in order to monitor the health, condition, and/or state of the user. The user may be unfamiliar with the process, procedures, and/or methods for pairing the health sensor with the wearable device (e.g., for establishing or setting up one or more communication channels between the health sensor and the wearable device).

The user may place a voice call to a caregiver, the call center 30 (e.g., a remote person or operator in the call center), etc., using the wearable device. For example, the wearable device may include a cellular communication interface (e.g., a communication interface used to communicate with a cellular network) and the user may place a voice call to the remote operator of the call center 30 using the cellular communication interface. A voice call may also refer to a voice-over-IP (VOIP) call. The user may indicate during the voice call that the user wishes to pair the health sensor (e.g., 18a) to the wearable device (e.g., 12a) of the user (e.g., 16a). The remote operator may provide instructions to the user (e.g., verbal instructions) to instruct the user to prepare the health sensor for pairing. For example, the remote operator may instruct the user to power or turn on the health sensor, or may instruct the user to activate a particular switch or button on the health sensor. After the user indicates that the health sensor is prepared for pairing, the remote operator may use the pairing module 27 to pair the health sensor with the wearable device. In one embodiment, the remote operator may provide user input to the pairing module 27 to indicate that a wearable device should be paired with a device (e.g., a health sensor). For example, the remote operator may receiving input from a remote operator indicating that the user of a wearable device wishes to pair the wearable device with an additional device (e.g., with a health sensor). The remote operator may provide the user input after speaking with the user via a voice call (as discussed above). In one embodiment, an automated system (e.g., an automated answering system) may instruct the user to prepare the health sensor for pairing. The user may provide input to the automated system (e.g., via button presses) to indicate that the health sensor is ready for pairing and the distributed cloud computing system 14 may initiate the pairing process as described above.

In one embodiment, pairing module 27 may transmit one or more instructions to the wearable device (e.g., 12a) to activate the communication interface that may be used to pair with the health sensor (e.g., 18a). For example, the pairing module 27 may transmit instructions to the health sensor 12a instructing the health sensor 12a to turn on and/or activate a Bluetooth communication interface. The pairing module may use a second communication interface of the wearable device to transmit the one or more instructions to the wearable device. For example, the pairing module 27 may use a cellular communication interface (e.g., a 3G communication interface, a 4G communication interface, etc.) to transmit the instructions to the wearable device. The wearable device may turn on the first communication interface (e.g., turn on Bluetooth) based on the instructions.

In another embodiment, the pairing module 27 may send one or more additional instructions instructing the wearable device to scan for devices (e.g., sensors, other computing devices, etc.) that are visible to the wearable device. For example, the pairing module 27 may instruct the wearable device 12a to perform a scan for Bluetooth devices that are visible to the wearable device 12a. One or more devices (e.g., health sensors or other devices) may be visible to a wearable device when the wearable device is able to communicate with the one or more devices. For example, a device (e.g., health sensor 18a) may be visible with to the wearable device (and vice versa) if the wearable device is able to transmit data to and/or receive data from the device. One or more devices may also be visible to the wearable device if the one or more devices are within a range of a communication interface of the wearable device (e.g., within 10 feet, 100 feet, 1 mile, etc.). The pairing module 27 may receive a list of one or more devices that are visible to the wearable device from the wearable device. For example, the wearable device may transmit information such as the model numbers, types, and/or identifiers of the one or more devices that are visible to the wearable device, to the pairing module 27.

In one embodiment, the pairing module 27 may analyze and/or process the list of one or more devices to identify a device that the wearable device is to be paired with. For example, the pairing module 27 may determine multiple types of devices (e.g., a headset, a speaker system, a mouse, a keyboard, a weight scale, a blood pressure sensor, etc.) are visible to the wearable device. The pairing module 27 may identify one or more devices (e.g., one or more health sensors) that the wearable device should pair with. For example, the paring module 27 may identify one or more health sensors that are supported by the distributed cloud computing system 14. The pairing module 27 may present the list of one or more health sensors that the wearable device should pair with, to the remote operator.

In one embodiment, the pairing module 27 may receive user input form the remote operator identifying a first device from the list of one or more devices. For example, as discussed above, the paring module 27 may receive a list of devices that are visible to the wearable device. The list may include identifiers for the devices on the list of devices. The identifiers may include information such as model numbers, types of the devices (e.g., computer, laptop, health sensor, speaker, headset, etc.), and/or other data that may be used to identify the devices that are visible to the wearable device. The remote operator may select one of the devices by providing the identifier for the selected devices to the pairing module. For example, selecting a device from the list of devices may provide the identifier for the selected device to the pairing module 27. In another example, the remote operator may provide the identifier to the paring module 27 (e.g., may input the identifier using a GUI). The pairing module 27 may also select one of the devices without input form the remote operator based on the identifiers for the devices. For example, the pairing module 27 may automatically identify devices that are health sensors.

In one embodiment, the pairing module 27 may access the database 37 to obtain instructions for pairing the first device with the wearable device. For example, the paring module 27 may access the database 37 to obtain instructions for pairing a weight sensor (e.g., a scale) with the wearable device 12a. The pairing module 27 may use an identifier for the selected device to obtain the instructions for pairing. For example, the pairing module 27 may use the model number, a name, serial number, etc., of the selected device to obtain the instructions for pairing from the database 37. The instructions for pairing may include commands, operations, access codes, passwords, etc., that may be used to pair the first device with the wearable device. In one embodiment, the pairing module 27 may access the instructions based on the identifier for the first device (e.g., based on a model number, a type, a MAC address, a serial number, etc.). In one embodiment, the instructions may include also include the identifier of the first device. This may allow the wearable device to identify which device the wearable device should pair with. In another embodiment, the instructions may cause the wearable device to automatically pair with the first device. For example, the instructions may cause the wearable device 12a to automatically pair with the health sensor 12a without user intervention or user input from the user 16a. After the wearable device is paired with the first device (e.g., with a health sensor), the wearable device may receive a confirmation (e.g., data, a message, etc.) from the wearable device to indicate that the wearable device is paired with the first device.

In one embodiment, after the wearable device is paired with an additional device (e.g., after wearable device 12a is paired with health sensor 18a), the wearable device may forward data received from the additional device to the distributed cloud computing system 14 and vice versa. For example, the wearable device may operate as a tunnel for data that is transmitted between the distributed cloud computing system 14 and the wearable device 12a, as discussed below in conjunction with FIG. 3.

Figure 2:
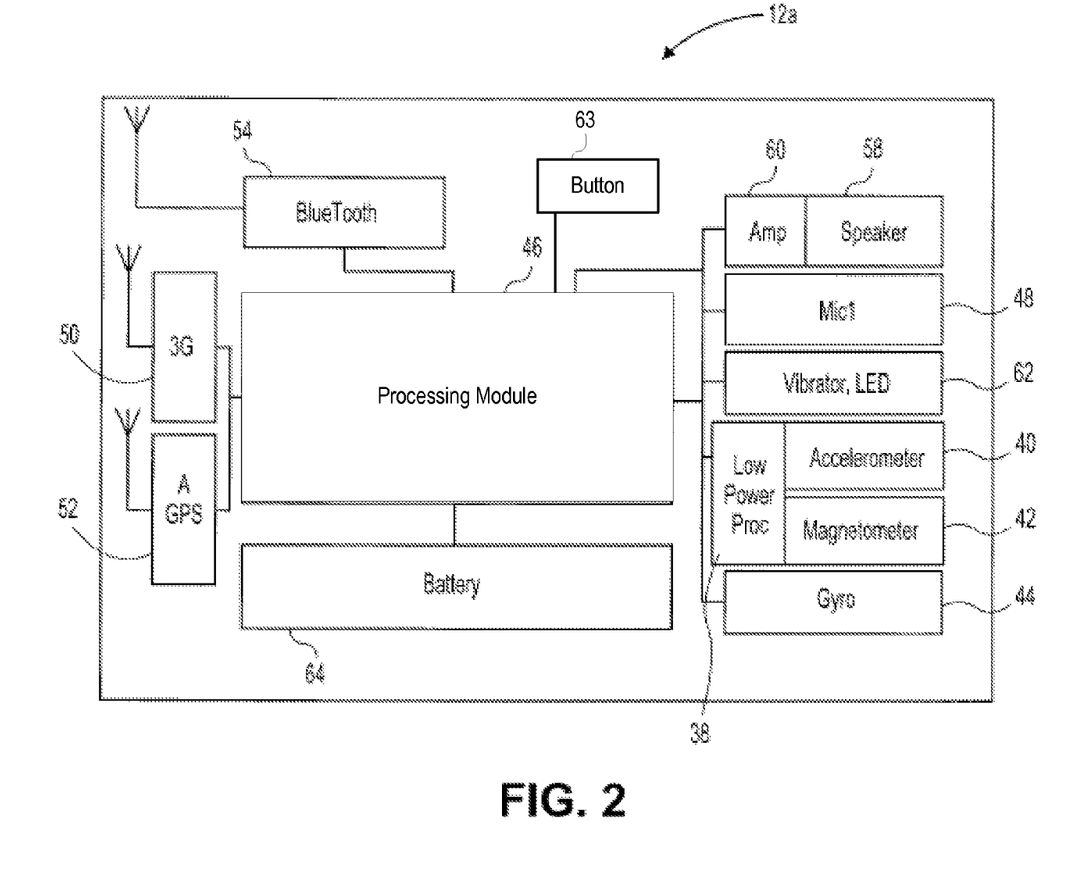
FIG. 2 is a block diagram illustrating one embodiment of a wearable device, according to one embodiment of the present disclosure.

FIG. 2 is a block diagram illustrating one embodiment of a wearable device 12a (e.g., wearable device 12a shown in FIG. 1). The wearable device 12a may include a low-power processor 38 communicatively connected to an accelerometer 40 (e.g., a two- or more-axis accelerometer) for detecting acceleration events (e.g., high, low, positive, negative, oscillating, etc.), a magnetometer 42 (preferably a 3-axis magnetometer) for assessing an orientation of the wearable device 12*a*, and a gyroscope 44 for providing a more precise determination of orientation of the wearable device 12*a*. The low-power processor 38 is configured to receive continuous or near-continuous real-time measurement data from the accelerometer 40, the magnetometer 42, and the gyroscope 44 for rendering tentative decisions concerning predefined user states. By utilizing the above components, the wearable device 12 is able to render these decisions in relatively low-computationally expensive, low-powered manner and minimize false positive and false negative errors. A processing module 46, such as the 3G IEM 6270 manufactured by Qualcomm®, includes a high-computationally-powered microprocessor element and internal memory that are adapted to receive the suspected fall events from the low-power processor 38 and to further correlate orientation data received from the optional gyroscope 44 with digitized audio data received from one or more microphones 48 (e.g., micro-electro-mechanical systems-based (MEMS) microphone(s)). The processing module 46 may also be referred to as a processing device. The audio data may include the type, number, and frequency of sounds originating from the user's voice, the user's body, and the environment.

The processing module 46 is also configured to receive data/commands from and/or transmit data/commands to the distributed cloud computing system 14 via a 3G, 4G, and/or other wireless protocol transceiver 50 over the cellular transmission network 20. The wireless protocol transceiver 50 may also be referred to as a communication interface. A communication interface may be software, hardware, or a combination of both that may be used to communicate data (e.g., transmit and/or receive data) with another device (e.g., a server, another computing device, a health sensor, etc.). The processing module 46 is further configured to communicate with and receive position data from an aGPS receiver 52, and to receive measurements from the external health sensors (e.g., sensors 18*a*-18*n* shown in FIG. 1) via a short-range Bluetooth transceiver 54 (or other equivalent short range transceiver such as a WiFi transceiver) or via a direct connection to one or more health sensors (e.g., the health sensors may be directly attached/coupled to the wearable device 12*a*). The aGPS receiver 52 and the Bluetooth transceiver 54 may also be referred to as communication interfaces.

In addition to recording audio data for fall analysis, the processing module 46 is further configured to permit direct voice communication between the user 16*a* and the PSAP (e.g. 9-1-1, an emergency response center, etc., not shown in the figures), a call center 30, first-to-answer systems 32 (e.g. a fire station, a police station, a physician's office, a hospital, etc.), or care givers and/or family 34 via a built-in speaker 58 and an amplifier 60. Either directly or via the distributed cloud computing system 14, the processing module 46 is further configured to permit the user 16*a* to conduct a conference connection with one or more of a PSAP, the call center 30, the first-to-answer systems 32, and/or care givers and/or family 34. The processing module 46 may receive/operate one or more input and output indicators 62 (e.g., one or more mechanical and touch switches (not shown), a vibrator, LEDs, etc.). The wearable device 12*a* also includes an on-board battery power module 64.

The wearable device 12*a* may also include a button 63. The button 63 may allow a user to provide user input to the wearable device 12*a*. For example, the user may press or push the button to initiate a voice call to one or more of a call center 30, first-to-answer systems 32 (e.g. a fire station, a police station, a physician's office, a hospital, etc.), or care givers and/or family 34. In another example, a user may use the button 63 to answer questions during a voice call (e.g., push the button 63 once for "yes" and push the button 63 twice for "no"). In another example, the user may indicate that the wearable device should start collecting data (e.g., datasets such as health data, audio data, location data, etc.) and/or send data to the distributed cloud computing system 14, using the button 63.

The wearable device 12*a* may also include empty expansion slots and/or connectors (not shown) to collect readings from other sensors (i.e., an inertial measurement unit, a pressure sensor for measuring air pressure or attitude, a heart rate sensor, blood perfusion sensor, temperature sensor), etc. These other sensors may be coupled to the device via the expansion slots and/or connectors to provide additional datasets or information to the distributed cloud computing system 14.

In one embodiment, the wearable device 12*a* may collect, gather, and/or obtain information using a variety of components. For example, the wearable device 12*a* may obtain orientation and/or movement data (e.g., information about how a user who is wearing the wearable device 12*a* has moved) using the accelerometer 40, the magnetometer 42, and/or the gyroscope 44. In another example, the wearable device 12*a* may determine the location (e.g., location data, such as GPS coordinates) of the wearable device 12*a* (and the user who is wearing or holding the wearable device 12*a*) using the aGPS receiver 52. In a further example, the wearable device may collect health data (e.g., heart rate, blood pressure, sugar levels, temperature, etc.) using sensors (not shown in the figures) which may be attached to the wearable device 12*a* and/or may communicate with the wearable device 12*a* using the Bluetooth transceiver 54. In yet another example, the wearable device 12*a* may obtain audio data (e.g., voice and/or sounds) using the microphone 48 or a plurality of microphones (now shown in the figures).

In one embodiment, the wearable device 12*a* may obtain and/or generate datasets (e.g., orientation/movement data, health data, location data, audio data) using these components and may transmit these datasets to the distributed cloud computing system 14. In another embodiment, the wearable device 12*a* may periodically transmit data sets to the distributed cloud computing system 14. For example, the wearable device 12*a* may transmit the datasets once every 5 seconds, or once every 30 seconds. In another embodiment, the wearable device 12*a* may transmit the datasets when certain criteria are met (e.g., when an accelerometer detects an acceleration above a certain threshold indicating a possible fall, or when the aGPS receiver determines that the wearable devices has left a certain location). In a further embodiment, the wearable device 12*a* may transmit datasets when a user input is received. For example, the wearable device 12*a* may send the datasets when the user presses or pushes the button 63, in order to initiate a voice call.

In one embodiment, the wearable device 12*a* may process the datasets, prior to providing the datasets to the distributed cloud computing system 14. For example, the wearable device 12*a* may process motion and/or orientation data to make an initial determination as to whether a user event (e.g., a fall or some other accident) has occurred. The distributed cloud computing system 14 may further process the datasets, in addition to the processing performed by the wearable device 12*a*. In another embodiment, the wearable device 12*a* may provide the datasets to the distributed cloud computing system 14 without first processing the datasets, and may allow the distributed cloud computing system 14 to process the datasets. In one embodiment, the distributed cloud computing system 14 may have more processing power (e.g., more CPUs) and may be better able to process and/or analyze the datasets than the wearable device 12a.

In one embodiment, the wearable device 12a may establish a voice call with a call center (as discussed above in conjunction with FIG. 1). The voice call may be initiated by the user of the wearable device or may be initiated by a remote operator in the call center. The wearable device 12a may receive a request for a list of one or more devices that are visible to the wearable device 12a. For example, the wearable device 12a may receive a request for the list via the wireless protocol transceiver 50 (via a first communication interface). The request for the list may include one or more instructions that may cause the wearable device 12a to activate the Bluetooth transceiver 54 (e.g., to activate a second communications interface). The wearable device 12a may use the Bluetooth transceiver 54 (e.g., the second communication interface) to pair with additional devices (e.g., with health sensors and/or other computing devices).

In one embodiment, the wearable device 12a may use the Bluetooth transceiver 54 to scan for devices (e.g., Bluetooth capable devices) that are visible to the Bluetooth transceiver 54 (e.g., that are within range of the Bluetooth transceiver 54). For example the wearable device 12a may receive instructions from a server (in a distributed cloud computing system) to scan for devices. The wearable device 12a may perform the scan and may store and/or record data about one or more devices that are visible to the wearable device 12a. For example the wearable device 12a may store and/or record identifiers (e.g., alphanumeric values, numerical values, serial number, a MAC address, a name, etc.) of the one or more devices. The wearable device 12a may transmit the list of the one or more devices that are visible, to the server. For example, the wearable device 12a may transmit a list of identifiers to the server using the wireless protocol transceiver 50.

In one embodiment, the wearable device 12a may receive one or more instructions to pair with a first device from the list of one or more devices. For example, the wearable device 12a may receive an identifier that may be used to identify the first device from the one or more devices that are visible to the wearable device 12a. The wearable device 12a may also receive commands, operations, access codes, passwords, etc., that the wearable device 12a may use to pair with the first device (e.g., pair with a health sensor). The wearable device 12a may pair with the first device using these instructions (e.g., using the identifiers, commands, operations, access codes, and/r passwords, etc.). The wearable device 12 may use the Bluetooth transceiver 54 to pair with the first device (e.g., to pair with the health sensor). After the first device is paired with the wearable device 12a (e.g., after a communication channel is established with the first device, the wearable device 12a may transmit a confirmation (e.g., a message, information and/or other data) to indicate that the wearable device 12a has successfully paired with the first device (e.g., to indicate that a Bluetooth pairing with a health sensor was successful).

In one embodiment, after the wearable device is paired with an additional device (e.g., after wearable device 12a is paired with health sensor 18a), the wearable device may forward data received from the additional device to the distributed cloud computing system 14 and vice versa. For example, the wearable device 12a may operate as a tunnel for data that is transmitted between the distributed cloud computing system 14 and the wearable device 12a, as discussed below in conjunction with FIG. 3.

Figure 3:
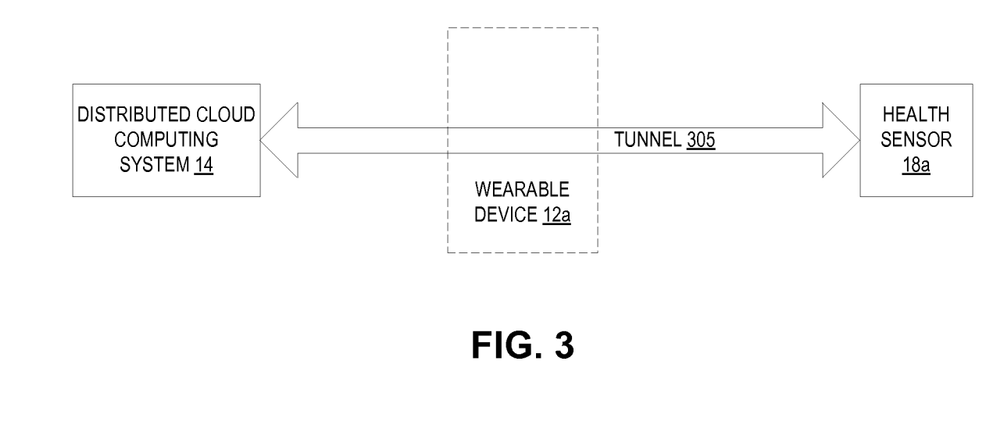
FIG. 3 is block diagram illustrating an example system architecture, according to another embodiment of the present disclosure.

FIG. 3 is block diagram illustrating an example system architecture 300, according to another embodiment of the present disclosure. The system architecture 300 includes a distributed cloud computing system 14, a wearable device 12a, and a health sensor 18a. As discussed above (in conjunction with FIGS. 1 and 2), the wearable device 12a may be paired with the health sensor 18a. For example, the wearable device 12a may be a Bluetooth capable device that is paired with the health sensor 18a which is also a Bluetooth capable device.

In one embodiment, a tunnel 305 (e.g., a logical communication channel) may be created or formed between the distributed cloud computing system 14 and the health sensor 18a when the health sensor 18a is paired with the wearable device 12a. The tunnel 305 may allow the health sensor 18a to communicate data to the distributed cloud computing system 14 and vice versa. The tunnel 305 may communicate data between the distributed cloud computing system 14 and the health sensor 18a via the wearable device 12a. For example, the wearable device 12a may operate as a proxy and may forward data from the distributed cloud computing system 14 to the wearable device 12a and vice versa. This may allow the wearable device 12a to operate with many different types of devices without having to process and/or understand the data that is provided by the different types of devices. For example, the health sensor 18a may be a new type of health sensor. The user may want to pair the health sensor 18a with the wearable device 12a. The wearable device 12a may not be able to process and/or analyze the type of data that the health sensor 18a generates. For example, the health sensor 18a may be a glucometer and the wearable device 12a may not be able to process data (e.g., glucose level measurements, sensor readings, etc.) from the health sensor 18a. The data from the health sensor 18a may be forwarded by the wearable device to the distributed cloud computing system 14 via the tunnel 305 (e.g., the wearable device 12a may forward the data to the distributed cloud computing system 14). The distributed cloud computing system 14 may process the data received from the health sensor 18a via the tunnel 305 (e.g., via the wearable device 12a) to determine the health or state of the user (e.g., to determine the glucose levels of the user). This allows the wearable device 12a to operate with the health sensor 18a and without the need for the wearable device 12a to understand that data (e.g., commands, sensor readings, operations, functions, protocols) of health sensor 18a. The tunnel 305 may also be used to provide data (e.g., information, commands, instructions, etc.) to directly to the health sensor 18a instead of providing the data to the wearable device 12a. For example, instead of instructing the wearable device 12a to instruct the health sensor 18a to perform a measurement, the distributed cloud computing system 14 may directly send the command to perform the measurement to the health sensor 18a via the tunnel 305 (e.g., via the wearable device 12a).

Figure 4:
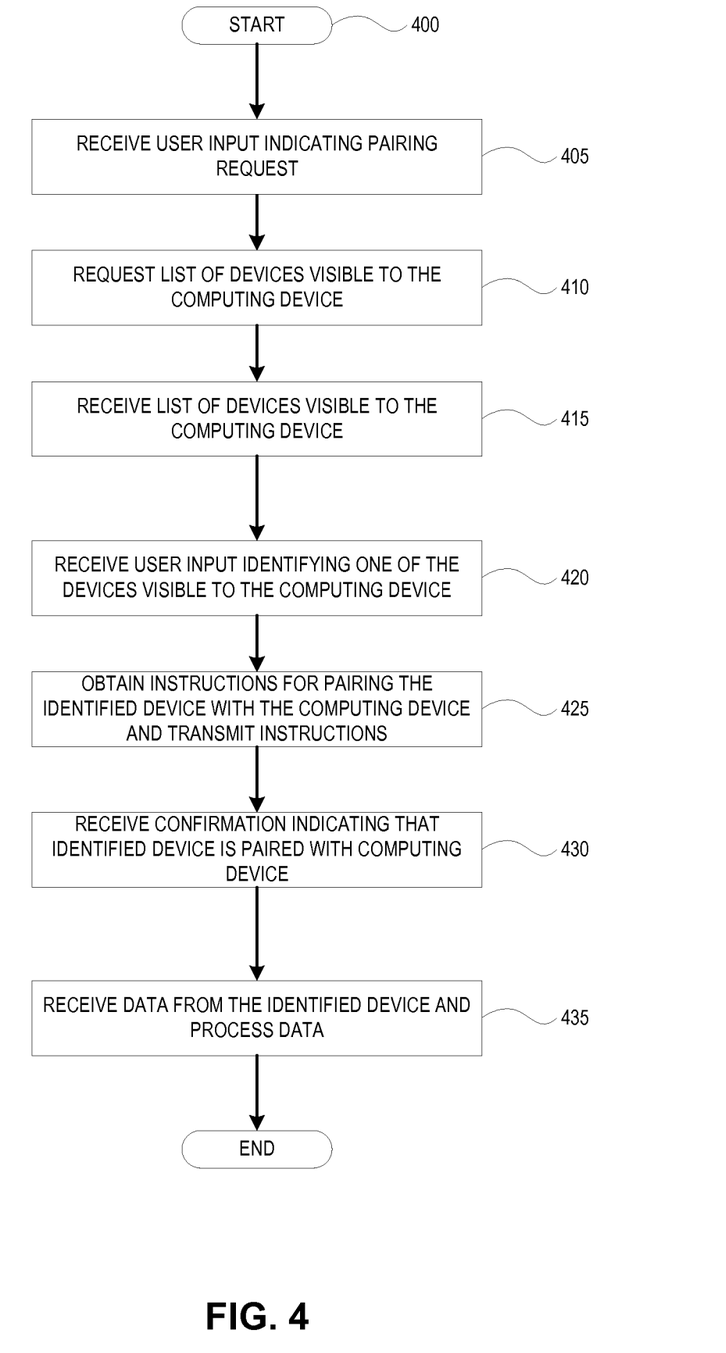
FIG. 4 is a flow diagram illustrating a method of pairing a first device with a computing device, according to one embodiment of the present disclosure.
Figure 5:
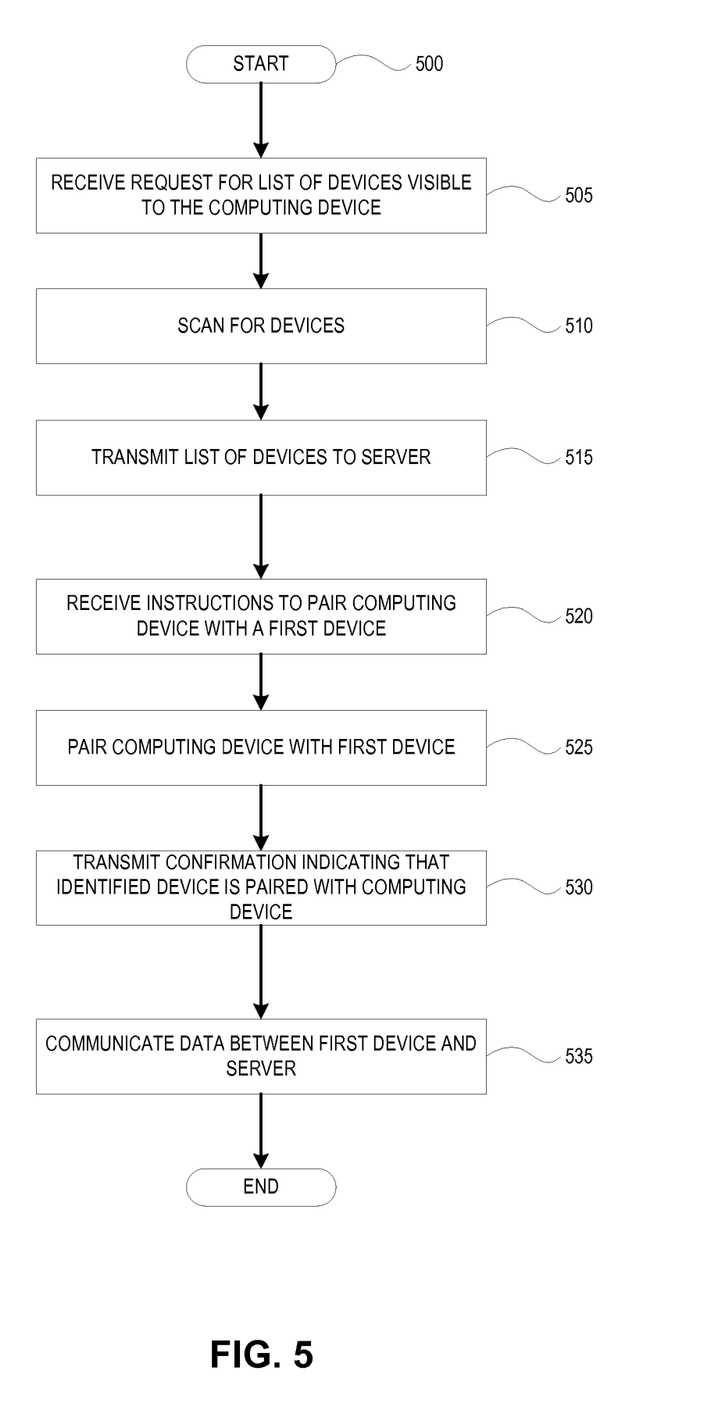
FIG. 5 is a flow diagram illustrating a method of pairing a first device with a computing device, according to another embodiment of the present disclosure.

FIGS. 4-5 are flow diagrams illustrating methods of pairing devices. For simplicity of explanation, the methods are depicted and described as a series of acts. However, acts in accordance with this disclosure can occur in various orders and/or concurrently and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

FIG. 4 is a flow diagram illustrating a method 400 of pairing a first device with a computing device, according to one embodiment of the present disclosure. The method 400 may be performed by processing logic that comprises hardware (e.g., circuitry, dedicated logic, programmable logic, microcode, etc.), software (e.g., instructions run on a processor to perform hardware simulation), or a combination thereof. In one embodiment, method 400 may be performed by a pairing module, as illustrated in FIG. 1.

Referring to FIG. 4 the method 400 begins at block 405 where the processing logic receives user input indicating a pairing request for the computing device. The computing device may be a wearable device (as illustrated in FIGS. 1 and 2). For example, the processing logic may receive user input from a remote operator indicating that a computing device should be paired with one or more other devices. At block 410, the processing logic may request a list of one or more devices that are visible to the computing device. For example, the processing logic may transmit instructions to the computing device that cause the computing device to activate or power on a first communication interface (e.g., a Bluetooth communication interface) and to scan for devices (e.g., scan for Bluetooth devices near the computing device). The processing logic may transmit these instructions to the computing device using a second communication interface (e.g., using a cellular communication interface). At block 415, the processing logic may receive a list of devices that are visible to the computing device from the computing device. For example, the processing logic may receive one or more identifiers (e.g., MAC address, a name, etc.) for the devices that are visible to the computing device.

At block 420, the processing logic may receive user input identifying a first device from the list of devices that are visible to the computing device. For example, the processing logic may receive user input from the remote operator selecting a first device from the list of devices that are visible to the computing device. The first device may be a health sensor (e.g., a scale, a glucometer, a thermometer, etc.) At block 425, the processing logic may obtain the instructions for pairing the first device with the computing device. For example, the processing logic may look up access codes, commands, passwords, etc., for pairing the first device with the computing device using an identifier for the first device. The processing logic may transmit these instructions to the computing device using the second communication interface. At block 430, the processing logic may optionally receive a confirmation (e.g., a message and/or other data) from the computing device indicating that the computing device has successfully paired with the first device. At block 435, the processing logic may communicate data (e.g., transmit and/or receive) between the server and the first device via a tunnel formed by the computing device (as discussed above in conjunction with FIG. 2). After block 435, the method 400 ends.

FIG. 5 is a flow diagram illustrating a method 500 of pairing a first device with a computing device, according to another embodiment of the present disclosure. The method 500 may be performed by processing logic that comprises hardware (e.g., circuitry, dedicated logic, programmable logic, microcode, etc.), software (e.g., instructions run on a processor to perform hardware simulation), or a combination thereof. In one embodiment, method 500 may be performed by a processing module, as illustrated in FIG. 2.

Referring to FIG. 5 the method 500 begins at block 505 where the processing logic receives a request for a list of devices that are visible to the computing device. The computing device may be a wearable device (as illustrated in FIGS. 1 and 2). The processing logic may receive this request using a first communication interface (e.g., a cellular communication interface). The request may include instructions that cause and/or instruct the processing logic to activate or power on a second communication interface (e.g., a Bluetooth communication interface). At block 510, the processing logic may scan for devices (e.g., scan for Bluetooth devices near the computing device). At block 515, the processing logic may transmit a list of devices that are visible to the computing device to a server (e.g., a server in a distributed cloud computing system). For example, the processing logic may transmit one or more identifiers (e.g., MAC address, a name, etc.) for the devices that are visible to the computing device.

At block 520, the processing logic may receive instructions for pairing the first device with the computing device. For example, the processing logic may receive an identifier, access codes, commands, passwords, etc., for pairing the first device with the computing device. The processing logic may receive these instructions to the computing device using the first communication interface. At block 525, the processing logic may pair the computing device with the first device based on the instructions for pairing. At block 530, the processing logic may optionally transmit a confirmation (e.g., a message and/or other data) from the computing device indicating that the computing device has successfully paired with the first device. At block 535, the processing logic may communicate data (e.g., transmit and/or receive) from the first device (e.g., a health sensor) to the server and vice versa (as discussed above in conjunction with FIG. 2). For example, the computing device may serve as a tunnel between the first device and the server and may forward data between the server and the first device (as discussed above in conjunction with FIG. 3). After block 535, the method 500 ends.

Figure 6:
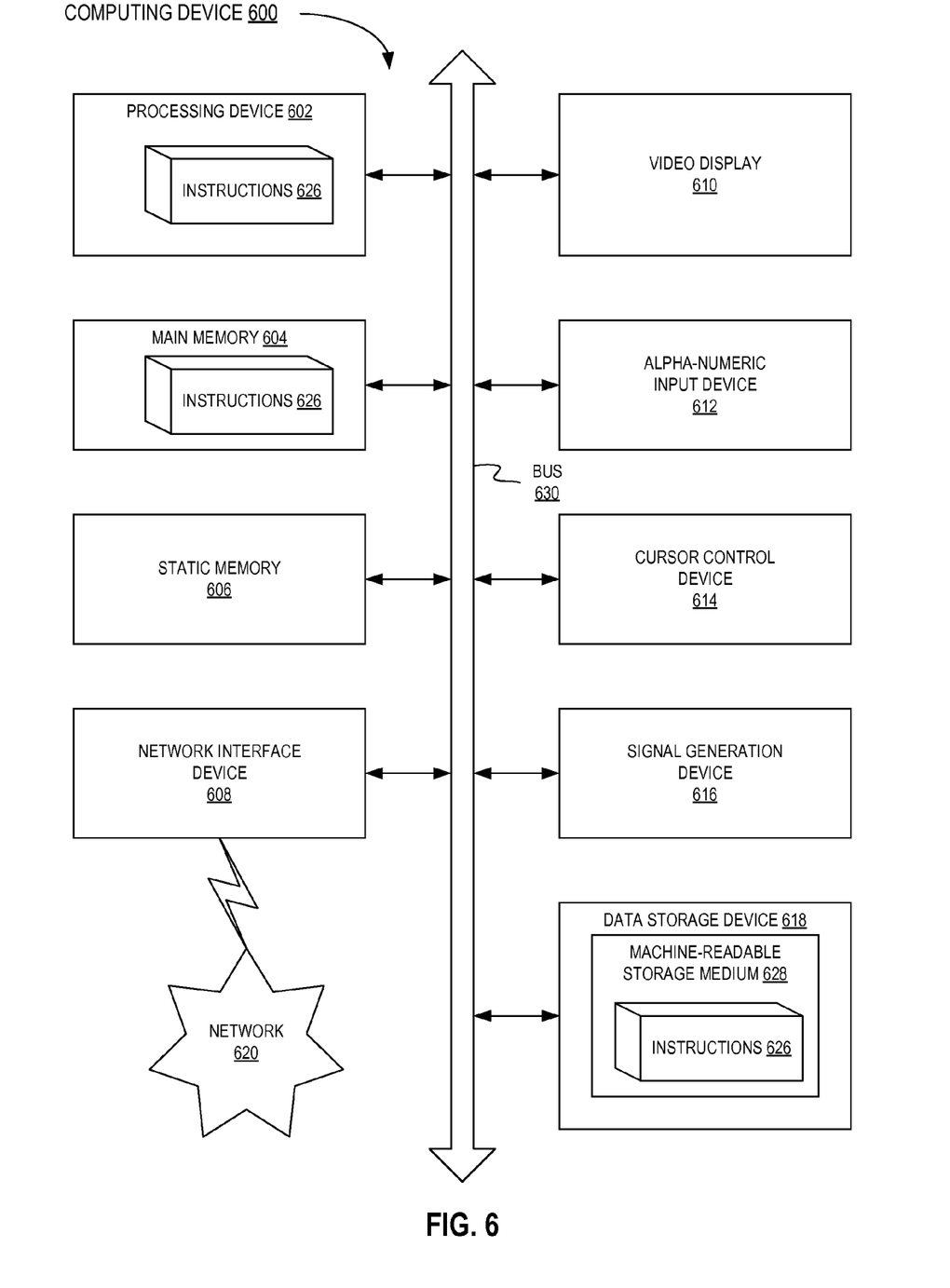
FIG. 6 is a block diagram of an exemplary computer system that may perform one or more of the operations described herein, according to one embodiment of the present disclosure.

FIG. 6 illustrates a diagrammatic representation of a machine in the example form of a computing device 600 within which a set of instructions, for causing the machine to perform any one or more of the methodologies discussed herein, may be executed. The computing device 600 may be a mobile phone, a smart phone, a netbook computer, a rackmount server, a router computer, a server computer, a personal computer, a mainframe computer, a laptop computer, a tablet computer, a desktop computer etc., within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server machine in client-server network environment. The machine may be a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. The example computing device may be a server (in a distributed cloud computing system) and/or may be a wearable device.

The example computing device 600 includes a processing device (e.g., a processor) 602, a main memory 604 (e.g., read-only memory (ROM), flash memory, dynamic random access memory (DRAM) such as synchronous DRAM (SDRAM)), a static memory 606 (e.g., flash memory, static random access memory (SRAM)) and a data storage device 618, which communicate with each other via a bus 630.

Processing device 602 represents one or more general-purpose processing devices such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and a signal generation device 616 (e.g., a speaker). In one embodiment, the video display unit 610, the alphanumeric input device 612, and the cursor control device 614 may be combined into a single component or device (e.g., an LCD touch screen).

The data storage device 618 may include a computer-readable storage medium 628 on which is stored one or more sets of instructions (e.g., instructions for a pairing module) embodying any one or more of the methodologies or functions described herein. The instructions 626 may also reside, completely or at least partially, within the main memory 604 and/or within the processing device 602 during execution thereof by the computing device 600, the main memory 604 and the processing device 602 also constituting computer-readable media. The instructions may further be transmitted or received over a network 620 via the network interface device 608.

While the computer-readable storage medium 628 is shown in an example embodiment to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media and magnetic media.

In the above description, numerous details are set forth. It will be apparent, however, to one of ordinary skill in the art having the benefit of this disclosure, that embodiments of the disclosure may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "receiving," "transmitting," "requesting," "obtaining," "processing," "scanning," "pairing," "forwarding," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the disclosure also relate to an apparatus for performing the operations herein. This apparatus may be specially constructed for the required purposes, or it may comprise a general purpose computer selectively activated or reconfigured by a computer program stored in the computer. Such a computer program may be stored in a non-transitory computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present disclosure is not described with reference to any particular programming language. It will be appreciated that a variety of programming languages may be used to implement the teachings of the disclosure as described herein.

The above description sets forth numerous specific details such as examples of specific systems, components, methods and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth above are merely examples. Particular implementations may vary from these example details and still be contemplated to be within the scope of the present disclosure.

It is to be understood that the above description is intended to be illustrative and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A method comprising:
   initiating a voice call with a remote operator in a call center;
   receiving instructions from the remote operator for a user to prepare a first device for pairing with a wearable device;
   receiving a first user input at the first device indicating a pairing request for the wearable device;
   after receiving the first user input, requesting, by a server, a list of one or more devices that are available for communication with the wearable device;
   receiving, at the server, the list of the one or more devices available for communication with the wearable device;
   receiving, at the server, a second user input identifying the first device from the list of one or more devices, wherein the first device comprises a health sensor; and
   transmitting, from the server to the wearable device and in response to the second user input identifying the first device, one or more instructions for use by the wearable device in pairing the health sensor with the wearable device.

2. The method of claim 1, wherein requesting the list of one or more devices comprises:
   transmitting a first instruction to the wearable device to activate a first communication interface, wherein the first communication interface is to be used by the wearable device to communicate with the health sensor; and
   transmitting a second instruction to the wearable device to perform a scan for the one or more devices.

3. The method of claim 1, wherein the second user input comprise an identifier for the health sensor.

4. The method of claim 3, further comprising:
   obtaining the one or more instructions based on the identifier.

5. The method of claim 1, further comprising:
   receiving data from the health sensor, wherein the data is forwarded from the health sensor via the wearable device; and
   processing the data received from the health sensor, wherein the data comprises health data of a user of the wearable device.

6. The method of claim 1, further comprising:
   receiving a confirmation from the wearable device, the confirmation indicating that the wearable device has successfully paired with the health sensor.

7. The method of claim 1, wherein the first user input is received based on the received instructions from the remote operator to prepare the first device for pairing with the wearable device.

8. The method of claim 7, wherein the wearable device comprises a second communication interface and wherein the voice call is established using the second communication interface.

9. An apparatus comprising:
   a memory to store data; and
   a processing device coupled to the memory, the processing device configured to:
   receive a request for a list of one or more devices, wherein the one or more devices are available for data communication with the apparatus;
   scan for available devices using a first communication interface, and prepare the list of one or more devices based on the scan result;
   transmit the list of one or more devices to a server using a second communication interface;
   receive, from the server, one or more instructions for use by the apparatus to pair with a first device from the list of one or more devices, wherein the first device comprises a health sensor; and
   pair with the heal sensor based on the one or more instructions.

10. The apparatus of claim 9, wherein the request for the list of one or more devices is received after a voice call is established using the second communication interface.

11. The apparatus of claim 9, wherein the processing device is configured to receive the request for the list of one or more devices by:
    receiving a first instruction to activate the first communication interface, wherein the first communication interface includes a Bluetooth communication interface used to communicate with the health sensor.

12. The apparatus of claim 9, wherein the processing device is further configured to:
    receive data from the health sensor; and
    forward the received data to the server.

13. The apparatus of claim 9, wherein the processing device is further configured to:
    receive first pairing instruction data from the server; and
    forward the received pairing instruction data to the health sensor.

14. A non-transitory computer readable storage medium having instructions that, when executed by a processing device, cause the processing device to perform operations comprising:
    requesting, by a server, a list of one or more user monitoring devices, wherein the one or more devices are available for data communication with a remote wearable computing device, wherein the remote wearable computing device is associated with a first user;
    receiving the list of one or more devices from the remote wearable computing device;
    receiving a remote user input identifying a first device from the list of one or more devices, wherein the remote user input is received from a user located remotely from the first user, and wherein the first device comprises a health sensor; and transmitting, from the server and to the remote wearable computing device, one or more instructions for use by the remote wearable computing device for pairing the health sensor with the remote wearable computing device.

15. The non-transitory computer readable storage medium of claim 14, wherein requesting the list of one or more user monitoring devices comprises:

transmitting a first instruction to the remote wearable computing device to activate a first communication interface, wherein the first communication interface is to be used by the remote wearable computing device to communicate with the health sensor; and transmitting a second instruction to the computing device to perform a scan for the one or more devices.

16. The non-transitory computer readable storage medium of claim 14, wherein the remote user input comprises an identifier for the health sensor.

17. The non-transitory computer readable storage medium of claim 16, the operations further comprising:

obtaining the one or more instructions based on the identifier.

18. The non-transitory computer readable storage medium of claim 14, the operations further comprising:

receiving data from the health sensor, wherein the data is forwarded from the health sensor via the remote wearable computing device; and processing the data received from the health sensor, wherein the data comprises health data of the first user associated with the remote wearable computing device.

19. The non-transitory computer readable storage medium of claim 14, the operations further comprising receiving a first user input in response to a voice call between a remote operator and a user of the remote wearable computing device, wherein the first user input indicates a user request for pairing the health sensor with the remote wearable computing device.

20. The method of claim 1, wherein the requesting, by the server, the list of one or more devices that are available for communication with the wearable device includes transmitting instructions to the wearable device to activate or power-up a communication interface and to scan for external devices.

* * * * *

UNITED STATES PATENT AND TRADEMARK OFFICE
CERTIFICATE OF CORRECTION

PATENT NO. : 9,526,420 B2  
APPLICATION NO. : 14/062688  
DATED : December 27, 2016  
INVENTOR(S) : Fish et al.

Page 1 of 1

It is certified that error appears in the above-identified patent and that said Letters Patent is hereby corrected as shown below:

In the Claims

In Column 18, Line 33, in Claim 9, delete "heal" and insert --health--, therefor In Column 18, Line 61, in Claim 14, after "device,", insert --and--

In Column 19, Line 15, in Claim 15, after "the", insert --remote wearable--

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*